United States Patent [19]

Kataoka et al.

[11] 4,167,525
[45] Sep. 11, 1979

[54] PROCESS FOR PREPARATION OF AROMATIC ACYL CHLORIDE

[75] Inventors: Yushin Kataoka; Shojiro Itoh; Masahiro Niwano, all of Niihama, Japan

[73] Assignee: Sumitomo Chemical Company, Limited, Osaka, Japan

[21] Appl. No.: 923,354

[22] Filed: Jul. 10, 1978

[30] Foreign Application Priority Data

Jul. 20, 1977 [JP] Japan ................................. 52-87807

[51] Int. Cl.$^2$ .......................... B01D 3/34; C07C 63/00
[52] U.S. Cl. ............................ 260/544 D; 260/544 P; 203/29; 203/35; 203/31; 203/96
[58] Field of Search ...................... 203/29, 31, 35, 34, 203/38, 96, 95, 97, 92, 93, 85, 76, 83, 79; 260/544 D, 544 P

[56] References Cited

U.S. PATENT DOCUMENTS

| | | | |
|---|---|---|---|
| 1,888,713 | 11/1932 | Britton et al. | 260/544 D |
| 1,906,761 | 5/1933 | Luthy et al. | 260/544 D |
| 2,048,768 | 7/1936 | Anderson | 260/544 D |
| 3,220,935 | 11/1965 | Nations et al. | 260/544 D |
| 4,091,017 | 5/1978 | Richtzenhain | 260/544 D |

*Primary Examiner*—Wilbur L. Bascomb, Jr.
*Attorney, Agent, or Firm*—Stevens, Davis, Miller & Mosher

[57] ABSTRACT

An aromatic acyl chloride is obtained with industrial advantages by reacting an aromatic carboxylic acid, phosphorus trichloride and chlorine, treating the reaction mixture comprising by-produced phosphorus pentachloride with at least one treating agent selected from water and phosphorus compounds to convert the phosphorus pentachloride into phosphorus oxychloride, and then subjecting the resulting reaction mixture to distillation to obtain the desired aromatic acyl chloride.

8 Claims, No Drawings

PROCESS FOR PREPARATION OF AROMATIC ACYL CHLORIDE

The present invention relates to a process for producing aromatic acyl chlorides.

More particularly, it relates to a process for producing aromatic acyl chlorides by reacting an aromatic carboxylic acid, phosphorus trichloride and chlorine.

In a known process for producing aromatic acyl chlorides, an aromatic carboxylic acid, phosphorus trichloride and chlorine are reacted to produce the aromatic acyl chlorides together with phosphorus oxychloride, as shown in the following chemical equation:

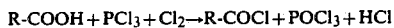

$$R\text{-}COOH + PCl_3 + Cl_2 \rightarrow R\text{-}COCl + POCl_3 + HCl$$

In this process, phosphorus trichloride is used in excess of the amount equivalent to the COOH group of aromatic carboxylic acid in order to obtain aromatic acyl chlorides in a high yield. Consequently, it is not avoidable that phosphorus pentachloride is produced as by-product by reaction between the excess phosphorus trichloride and chlorine supplied to the reaction system after chlorination of aromatic carboxylic acid is completed.

The vapor pressure of phosphorus pentachloride is lower than that of phosphorus oxychloride and higher than that of the aromatic acyl chloride, and besides phosphorus pentachloride is sublimable. Consequently, the aromatic acyl chloride cannot be separated from the reaction mixture by a conventional distillation without blocking of distillation equipments by phosphorus pentachloride, thus making the continuous stable operation of distillation impossible.

In order to solve this drawback, Japanese Patent Publication (unexamined) No. 135937/1974 discloses a process wherein phosphorus pentachloride produced as by-product is first converted to thionyl chloride and phosphorus oxychloride by the action of sulfur dioxide gas and then the aromatic acyl chloride is recovered by distillation. But, this process produces thionyl chloride so that it has the drawback that thionyl chloride needs to be recovered and treated.

For the reasons as described above, the invertors extensively studied to develop a process having no drawbacks described above, that is, a process how to treat phosphorus pentachloride remaining in the reaction mixture so as not to produce a by-product. An object of the present invention is to provide a process for producing aromatic acyl chlorides by reacting an aromatic carboxylic acid, phosphorus trichloride and chlorine followed by distillation of the reaction mixture characterized by producing the aromatic acyl chlorides without causing blocking on distillation and formation of troublesome by-products.

The object can be accomplished by providing a process for preparing an aromatic acyl chloride, comprising reacting an aromatic carboxylic acid, phosphorus trichloride and chlorine, treating the reaction mixture comprising by-produced phosphorus pentachloride with at least one treating agent selected from the group consisting of water and phosphorus compounds to convert the phosphorus pentachloride into phosphorus oxychloride, and then subjecting the resulting reaction mixture to distillation to obtain phosphorus oxychloride and successively the desired aromatic acyl chloride.

The aromatic carboxylic acid used in the present invention means a group of compounds in which at least one carboxylic group is directly connected to the aromatic nucleus. For example, there may be given benzoic acid, phthalic acid, isophthalic acid, terephthalic acid, hemimellitic acid, trimellitic acid, trimellitic anhydride and the like. But the present invention is not limited to these examples.

As to the reaction among the aromatic carboxylic acid, phosphorus trichloride and chlorine, there is no particular limitation except that phosphorus trichloride and chlorine are used in excess of the amount equivalent to the COOH group of the aromatic carboxylic acid. As to phosphorus trichloride, however, the equivalent ratio of phosphorus trichloride to COOH group of aromatic carboxylic acid is generally 1 or more, preferably 1.01 to 1.30. When the ratio is below this range, a state wherein phosphorus trichloride is present in excess can not be kept until the end of the reaction, thus resulting in a reduction in yield. When the ratio is beyond this range, there are no particular difficulties. But, too large ratios are not practical since the amount of the phosphorus compound capable of converting phosphorus pentachloride to phosphorus oxychloride, and/or water becomes too large. Also, the amount of chlorine is approximately equivalent to that of phosphorus trichloride.

The reaction temperature is not particularly limited as far as a liquid portion in the reaction mixture is allowed to exist, and it is preferably 20° to 130° C. Also, the reaction pressure is not particularly limited, but it is generally 1 to 20 atmospheres. The reaction time is not particularly limited, and varies with the rate of introduction of chlorine. The reaction may be carried out in the presence or absence of a solvent such as phosphorus oxychloride and tetrachloromethane.

The reaction mixture obtained by the foregoing reaction comprises aromatic acyl chloride, phosphorus oxychloride, hydrogen chloride, chlorine and phosphorus pentachloride. The reaction mixture thus obtained is then subjected to the treatment of phosphorus pentachloride characteristic of the present invention.

As the treating agent, i.e. as the phosphorus compound capable of converting phosphorus pentachloride to phosphorus oxychloride, and/or water used in the present invention, there may be given phosphorus pentoxide, a reaction product resulting from water and phosphorus pentoxide, reaction product from water and phosphorus oxychloride, reaction product from phosphorus pentoxide and phosphorus oxychloride, reaction product from water, phosphorus pentoxide and phosphorus oxychloride, and water. The reaction product resulting from water and phosphorus pentoxide referred to herein means those which are obtained by mixing water and phosphorus pentoxide in an optional ratio, and includes, for example, phosphoric acid, pyrophosphoric acid, tripolyphosphoric acid, polyphosphoric acid, metaphosphoric acid and mixtures thereof. The reaction product resulting from water and phosphorus oxychloride, and that resulting from water, phosphorus pentoxide and phosphorus oxychloride referred to herein mean mixtures containing polyphosphoryl chloride and/or a compound having phosphoric radical,

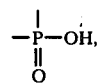

and, in some cases, each material unreacted. The reaction product resulting from phosphorus pentoxide and phosphorus oxychloride referred to herein means mixtures containing polyphosphoryl chloride and, in some cases, each material unreacted. Of these, the reaction produce resulting from water and phosphorus oxychloride, that from phosphorus pentoxide and phosphorus oxychloride, and that from water, phosphorus pentoxide and phosphorus oxychloride give particularly a desirable effect with no particular reduction of yield and little content of tarry matters.

The reaction between the treating agent and phosphorus pentachloride may be assumed to proceed as follows:

$$P^V-O-P^V + PCl_5 \rightarrow 2P^VCl + POCl_3$$

$$P^V-OH + PCl_5 \rightarrow P^VCl + POCl_3 + HCl$$

$$H_2O + PCl_5 \rightarrow POCl_3 + 2HCl$$

Wherein $P^V$ is a penta-valent phosphorus atom.

That is, phosphorus pentachloride is converted to phosphorus oxychloride by addition of the treating agent.

The amount of the treating agent is satisfactorily more than the amount necessary to substantially eliminate phosphorus pentachloride present in the reaction mixture. And, it is preferably 0.8 or more by gram equivalent of $P^V-O-P^V$ groups and OH groups contained in the substance, based on the mole number of phosphorus pentachloride present in the reaction mixture. Particularly preferably, it is within the range of 1.0 to 10. Too small amounts and too large amounts of the treating agent are not desirable because the former fails to remove phosphorus pentachloride, because the latter increases the amount of tarry matters.

The conditions of the treatment are not particularly limited, but the treatment is carried out usually at a temperature of room temperature to a boiling point of the reaction mixture, favorably from 30° to 130° C., for 0.1 to 10 hours. Also, it is desired to stir the treatment system, so that the treatment is accelerated.

The reaction mixture thus treated is then subjected to distillation by usual manners, whereby the aromatic acyl chloride can be recovered. According to the foregoing process of the present invention, the production of aromatic acyl chlorides can be achieved without blocking of distillation equipments encountered in distillation of the untreated reaction mixture, and without using special distillation equipments. Further, the process of the present invention has the remarkable advantage that it produces newly no by-product unlike the well-known process wherein the reaction mixture is treated with sulfur dioxide gas. Accordingly, the present invention has extremely a large industrial value.

The present invention will be illustrated in more detail with reference to the following examples, but the present invention is not limited to these examples.

EXAMPLE 1

A 500-ml flask was equipped with a chlorine-introducing pipe, electric stirrer, thermometer and cooler through which o-dichlorobenzene cooled to 5° to 15° C. was circulated. The outlet of the cooler was connected to a trap cooled to about −20° C. with carbon tetrachloride/dry ice. 226.6 g (1.65 moles) of phosphorus trichloride and 183.2 g (1.50 mole) of benzoic acid were charged in the flask. Chlorine was then blown into the flask at a rate of 100 ml/min with stirring while maintaining the inner temperature of the flask at 60° C. in an oil bath, and reaction was continued for 340 minutes. Thereafter, 16.8 g of phosphorus trichloride collected in the trap was returned to the flask, and chlorine was blown into the flask for further 30 minutes at a rate of 100 ml/min. The reaction mixture was a uniform liquid slightly yellow colored. One milliliter of the reaction mixture was sampled and analyzed for phosphorus pentachloride contained therein. As a result, it was found that 0.10 mole of phosphorus pentachloride was present.

30.7 g of phosphorus oxychloride and 4.9 g (0.05 moles, 0.15 g equivalent) of phosphoric acid were mixed and reacted at room temperature for 20 minutes with stirring. The resulting treating agent was added to the foregoing reaction mixture, followed by treatment at 105° C. for 60 minutes with stirring. One milliliter of the resulting mixture was sampled and analyzed for phosphorus pentachloride. But phosphorus pentachloride was not detected.

After phosphorus oxychloride was separated from the thus treated reaction mixture by distillation under atmospheric pressure, the residual matter was vacuum-distilled at 83° C. and 15 mmHg to obtain colorless and transparent benzoyl chloride in a yield of 97.5%. On distillation, attachment of phosphorus pentachloride to the distillation apparatus was not observed.

This result was shown in Exp. No. 1 in Table 1.

Further, the production of benzoyl chloride was repeated in the same manner as in Exp. No. 1 except that the treating agent was changed. This result is shown in Table 1.

No treatment of the reaction mixture with the treating agent was also shown in Table 1.

Table 1

| Exp. No. | Treating agent | | Conditions for production of treating agent | Amount added: equivalent ratio (based on PCl$_5$) | Phosphorus pentachloride content in reaction mixture | | Attachment of phosphorus pentachloride to distilling apparatus |
|---|---|---|---|---|---|---|---|
| | | | | | Before treatment (mole) | After treatment (mole) | |
| 1 | Phosphoric acid Phosphorus oxychloride | 4.9g 30.7g | Room temperature, 20 min. | 1.5 | 0.10 | N.D.* | Not observed |
| 2 | Water Phosphorus oxychloride | 3.6g 61.3g | 80° C., 30 min. | 2.0 | 0.10 | N.D. | '' |
| 3 | Phosphorus pentoxide | 15.6g | 105° C., 60 min | 3.0 | 0.11 | N.D. | '' |

Table 1-continued

| Exp. No. | Treating agent | Conditions for production of treating agent | | Amount added: equivalent ratio (based on PCl₅) | Phosphorus pentachloride content in reaction mixture | | Attachment of phosphorus pentachloride to distilling apparatus |
|---|---|---|---|---|---|---|---|
| | | | | | Before treatment (mole) | After treatment (mole) | |
| 4 | Phosphorus oxychloride | 50.6g | 100° C., 30 min. | 2.5 | 0.10 | N.D. | " |
| | Water | 0.9g | | | | | |
| | Phosphorus pentoxide | 9.5g | | | | | |
| 5 | Phosphorus oxychloride | 61.3g | | 4.0 | 0.09 | N.D. | " |
| | Phosphorus pentoxide | 17.0g | | | | | |
| 6 | Polyphosphoric acid | 6.7g | | 1.5 | 0.11 | N.D. | " |
| 7 | Phosphorus pentoxide | 3.2g | Room temperature, 5 min | 1.0 | 0.10 | N.D. | " |
| | Water | 0.6g | | | | | |
| 8 | Metaphoshoric acid | 8.8g | | 2.0 | 0.11 | N.D. | " |
| 9 | Pyrophosphoric acid | 5.1g | | 1.2 | 0.12 | N.D. | " |
| 10 | Water | 1.8g | | 1.0 | 0.10 | N.D. | " |
| Comparative example | Not used | — | | 0 | 0.11 | — | Observed |

*N.D.: Not detected

EXAMPLE 2

315.9 g (2.3 moles) of phosphorus trichloride and 166.1 g (1.0 mole) of isophthalic acid were charged in the same apparatus as in Example 1. Chlorine was then blown into the flask for 290 minutes with stirring at a rate of 160 ml/min while maintaining the inner temperature of the flask at 50° C. Phosphorus pentachloride contained in the reaction mixture was analyzed, and it was found 0.07 moles. 46.0 g of phosphorus oxychloride and 1.8 g (0.1 mole) of water were mixed and reacted at 70° C. for 30 minutes with stirring. The resulting treating agent was added to the foregoing reaction mixture, followed by treatment at 80° C. for 20 minutes with stirring. The reaction mixture thus treated was analyzed for phosphorus pentachloride, but phosphorus pentachloride was not detected.

After phosphorus oxychloride was separated from the thus treated reaction mixture by distillation under reduced pressure, the residual matter was vacuum-distilled at 143° C. and 15 mmHg to obtain isophthaloyl chloride (m.p. 43.5°–44.0° C.) in a yield of 97.0%. On distillation, attachment of phosphorus pentachloride to the distilling apparatus was not observed.

EXAMPLE 3

288.4 g (2.1 mole) of phosphorus trichloride and 166.1 g (1.0 mole) of terephthalic acid were charged in the same apparatus as in Example 1. Chlorine was then blown into the flask for 430 minutes with stirring at a rate of 100 ml/min while maintaining the inner temperature of the flask at 70° C. Thereafter, 19.5 g of phosphorus trichloride collected in the trap was returned to the flask, and chlorine was blown into the flask for further 40 minutes at a rate of 100 ml/min. Phosphorus pentachloride contained in the reaction mixture was analyzed, and it was found 0.05 moles. 4.7 g (0.10 g equivalent) of phosphorus pentoxide was added to the foregoing reaction mixture, followed by treatment at 105° C. for 2 hours with stirring. The reaction mixture thus treated was analyzed for phosphorus pentachloride, but phosphorus pentachloride was not detected.

After phosphorus oxychloride was separated from the thus treated reaction mixture by distillation under reduced pressure, the residual matter was vacuum-distilled at 140° C. and 15 mmHg to obtain terephthaloyl chloride (m.p. 83°–84° C.) in a yield of 96.6%. On distillation, attachment of phosphorus pentachloride to the distilling apparatus was not observed.

What is claimed is:

1. A process for preparing an aromatic acyl chloride, comprising reacting an aromatic carboxylic acid, phosphorus trichloride and chlorine, treating the reaction mixture comprising by-produced phosphorus pentachloride with at least one treating agent selected from the group consisting of water and phosphorus compounds to convert the phosphorus pentachloride into phosphorus oxychloride, and then subjecting the resulting reaction mixture to distillation to obtain phosphorus oxychloride and successively the desired aromatic acyl chloride.

2. The process according to claim 1, wherein the treating agent is phosphorus pentoxide, a reaction product resulting from water and phosphorus pentoxide, a reaction product resulting from water and phosphorus oxychloride, a reaction product resulting from phosphorus pentoxide and phosphorus oxychloride, or a reaction product resulting from water, phosphorus pentoxide and phosphorus oxychloride.

3. The process according to claim 1, the amount of the phosphorus compound and/or water is 0.8 or more by gram equivalent of $P^V$—O—$P^V$ groups and OH groups contained in said phosphorus compound and/or water, based on the mole number of phosphorus pentachloride present in the reaction mixture wherein $P^V$ is a penta-valent phosphorus atom.

4. The process according to claim 1, wherein the treating is conducted at a temperature of room temperature to a boiling point of the reaction mixture for 0.1 to 10 hours.

5. The process according to claim 1, wherein the aromatic carboxylic acid is benzoic acid, phthalic acid, isophthalic acid, terephthalic acid, hemimellitic acid, trimellitic acid or trimellitic anhydride.

6. The process according to claim 1, wherein the equivalent ratio of phosphorus trichloride to COOH group of the aromatic carboxylic acid is 1.01 to 1.30.

7. The process according to claim 1, wherein the amount of chlorine is approximately equivalent is phosphorus trichloride.

8. The process according to claim 1, wherein the reacting is conducted at a temperature of 20° to 130° C.

* * * * *